(12) United States Patent
Kim et al.

(10) Patent No.: US 8,691,973 B2
(45) Date of Patent: Apr. 8, 2014

(54) METHOD OF PRODUCING CHITOSAN SCAFFOLD HAVING HIGH TENSILE STRENGTH AND CHITOSAN SCAFFOLD PRODUCED USING THE METHOD

(75) Inventors: Chun-Ho Kim, Seoul (KR); Seung-Jae Lee, Seoul (KR); Jin-Ik Lim, Seoul (KR); Youngsook Son, Seoul (KR)

(73) Assignee: Korea Institute of Radiological & Medical Sciences (KR)

(*) Notice: Subject to any disclaimer, the term of this patent is extended or adjusted under 35 U.S.C. 154(b) by 649 days.

(21) Appl. No.: 12/157,120

(22) PCT Filed: Feb. 21, 2007

(86) PCT No.: PCT/KR2007/000908
§ 371 (c)(1),
(2), (4) Date: Jun. 9, 2008

(87) PCT Pub. No.: WO2007/111416
PCT Pub. Date: Oct. 4, 2007

(65) Prior Publication Data
US 2008/0242850 A1    Oct. 2, 2008

(30) Foreign Application Priority Data
Mar. 28, 2006    (KR) .................. 10-2006-0027980

(51) Int. Cl.
C08B 37/08    (2006.01)

(52) U.S. Cl.
USPC ............... 536/55.3; 536/20; 514/55; 424/488

(58) Field of Classification Search
USPC ................... 536/20, 55.3; 514/55; 424/488
See application file for complete search history.

(56) References Cited

U.S. PATENT DOCUMENTS 5,525,710 A * 6/1996 Unger et al. ................. 536/18.7
2003/0119157 A1 * 6/2003 Jeong et al. .................. 435/178

FOREIGN PATENT DOCUMENTS

| KR | 10-2001-0063154 | 7/2001 |
| KR | 10-2004-0019460 | 3/2004 |
| KR | 10-2005-0039960 | 5/2005 |
| KR | 10-2006-0134346 | 12/2006 |
| WO | 01/46266 | 6/2001 |

OTHER PUBLICATIONS

Ma et al. Biomaterials, 2003, 24, p. 4833-4841.*
Ho et al., Biomaterials, 2004, 25, p. 129-138.*
Ferro Fontan et al., J. Food Technol., 1981, 16, 21-30.*
Shepherd et al., Glycoconjugate J., 1997, 13, p. 535-542.*
Ma et al., Biomaterials, 2001, 22, p. 331-336.*
Teagarden et al., Eur. J. Pharm. Sci., 2002, 15, p. 115-133.*
International Search Report for PCT/KR2007/000908 dated May 22, 2007.
Written Opinion for PCT/KR2007/000908 dated May 22, 2007.
Il Juhn Roh et al., "Fabrication of a pure porous chiosan bead matrix: influences of phase separation on the microstructure", Journal of Biomaterial Sciences Polymer Edn. vol. 13, No. 7, pp. 769-782, Published 2002.

* cited by examiner

*Primary Examiner* — Layla Bland
*Assistant Examiner* — Jonathan S Lau
(74) *Attorney, Agent, or Firm* — Cantor Colburn LLP

(57) ABSTRACT

Provided are a method of producing a porous chitosan scaffold, the method including: providing an aqueous acidic solution having chitosan and a solvent which does not dissolve the chitosan; and freeze-drying the aqueous acidic solution, wherein the solvent is selected from the group consisting of a C3-C8 aliphatic alcohol having one hydroxy group, ethylene glycol monoethylether, ethylene glycol monobutylether, dioxane, tetrahydrofuran, dimethylcarbonate, acetone and acetonitrile, and a chitosan scaffold produced using the method.

7 Claims, 7 Drawing Sheets
(4 of 7 Drawing Sheet(s) Filed in Color)

C  D

E  F

A    B

A    B

METHOD OF PRODUCING CHITOSAN SCAFFOLD HAVING HIGH TENSILE STRENGTH AND CHITOSAN SCAFFOLD PRODUCED USING THE METHOD

CROSS-REFERENCE TO RELATED PATENT APPLICATION

This application claims the benefit of Korean Patent Application No. 10-2006-0027980, filed on Mar. 28, 2006, in the Korean Intellectual Property Office, the disclosure of which is incorporated herein in its entirety by reference.

BACKGROUND OF THE INVENTION

1. Field of the Invention

The present invention relates to a method of producing a chitosan scaffold having high tensile strength and a chitosan scaffold produced using the method.

2. Description of the Related Art

Chitosan is a linear amino polysaccharide having β-D-glucosamine (2-amino-2-deoxy-β-D-glucan) repeating units that are linked to each other via a (1→4) linkage. Chitosan can be prepared, for example, by deacetylating chitin with alkali. Chitosan is generally characterized by the degree of deacetylation, and is dissolved not in water, but in most of the acidic mediums having pH levels at or lower than 6.9.

Conventionally, there are various methods of preparing a scaffold for culturing cells using chitosan as a based material. For example, Korean Patent No. 0375422 discloses a porous bead-type matrix for cell culture having relatively uniform pores having a size in the range of 30 to 150 μm on the surface of and inside the matrix, wherein a material that is used to form the porous bead-type matrix is chitosan, water-soluble chitosan, or a mixture thereof, and cells to be cultured are attached to and grow on the surface of the matrix or the pore inside the matrix. In this case, a method of preparing porous chitosan beads for culturing cells includes preparing one of a chitosan solution by dissolving chitosan in an aqueous acetic acid solution, a water-soluble chitosan solution by dissolving water-soluble chitosan in deionized water, or a mixture of the chitosan solution and the water-soluble chitosan solution, adding the solution drop wise to an organic solvent at a low temperature in the range of −65 to −5° C. to obtain beads, and freeze-drying the chitosan beads. Korean Patent No. 0546793 also discloses a method of preparing a foam dressing using chitosan including: obtaining a chitosan structure as foam dressing by freeze-drying an aqueous acidic solution of chitosan having glycerol; completely removing an acid by neutralizing and washing the chitosan structure sequentially with a 95% or higher pure ethanol, a 70% or higher ethanol solution, a 50% or higher ethanol solution, and water or a buffer solution; and freeze-drying the neutralized chitosan structure.

In a porous scaffold that is used in tissue engineering and cell culture, various elements, such as elements used to attach cells to the porous scaffold, essential ingredients used to culture the attached cells, and metabolites resulted from cell growth, need to flow into and out of the porous scaffold. Examples of such elements may include cytokine, hormones, and medium ingredients. Cells or tissues in addition to various elements should easily flow into the porous scaffold and be easily attached to the porous scaffold for the cell or tissue growth. Thus, the porous scaffold needs to have a size distribution of pores providing conditions proper for cell inflow, attachment and growth, such as proper surface area, and facility in supplying oxygen and nutrients. For this, the porous scaffold needs to have excellent interconnectivity between pores.

However, according to such conventional technologies, pores in inner walls of the chitosan structure are formed in tubal shapes due to film-forming ability of the chitosan. Thus, the chitosan structure has disadvantages of not having high tensile strength or having nonuniform pore size. Particularly, when the porous scaffold has a pore size of 120 μm or greater, cells are not easily attached to the porous scaffold and pass through the pores during cell inoculation to attach cells to the porous scaffold. Further, since interconnectivity between tubal pores is not good enough, efficiency of cell attachment decreases during cell inoculation, and efficiency of transferring essential ingredients for cell attachment and growth, metabolites and cells between pores decreases. Thus, the tubal pores are not suitable for carriers used in tissue engineering, cell culture, and drug delivery.

Accordingly, a method of producing a chitosan scaffold having high tensile strength, uniform size distribution of pores, and excellent interconnectivity between the pores still needs to be developed.

SUMMARY OF THE INVENTION

The present invention provides a method of producing a chitosan scaffold having high tensile strength, uniform size distribution of pores and excellent interconnectivity between the pores.

The present invention also provides a chitosan scaffold produced using the method.

According to an aspect of the present invention, there is provided a method of producing a porous chitosan scaffold, the method including:

providing an aqueous acidic solution including chitosan and a solvent which does not dissolve the chitosan; and freeze-drying the aqueous acidic solution, wherein the solvent which does not dissolve the chitosan is selected from the group consisting of a C3-C8 aliphatic alcohol having one hydroxy group, ethylene glycol monoethylether, ethylene glycol monobutylether, dioxane, tetrahydrofuran, dimethylcarbonate, acetone and acetonitrile.

Here, chitosan is a linear amino polysaccharide having β-D-glucosamine (2-amino-2-deoxy-β-D-glucan) repeating units which are linked to each other via a (1→4) linkage. Chitosan can be prepared by deacetylating chitin with alkali, but the method of preparing chitosan is not limited thereto. Chitosan is generally characterized by the degree of deacetylation, and is not dissolved in water, but in most of the acidic mediums having pH levels at or lower than 6.9 (between pH 6.2 and 6.9 depending on the amount of amine in chitosan). The chitosan that is used in the present invention is not limited. For example, chitosan derivatives prepared by modifying a chitosan can also be used in addition to the chitosan capable of dissolving in a diluted aqueous acidic solution. Examples of the chitosan may include a water-soluble chitosan prepared by uniform deacetylation of chitin and capable of dissolving in deionized water, an N-acyl chitosan derivative prepared by N-acylation, and an N-carboxyalkyl chitosan derivative to which a carboxyalkyl group is introduced. The chitosan used in the present invention may have a degree of deacetylation ranging from 40 to 100% and a molecular weight ranging from 13,000 to 1,000,000.

The solvent which does not dissolve the chitosan (nonsolvent) may be a C1-C8 alcohol having one hydroxy group, ethylene glycol monoethylether, ethylene glycol monobutylether, dioxane, tetrahydrofuran, dimethylcarbonate, acetone or acetonitrile, preferably a C2-C8 aliphatic alcohol having one hydroxy group, and more preferably a C3-C8 aliphatic alcohol having one hydroxy group. The amount of the nonsolvent may be in the range of 0.001 to 30% (v/v). When the amount of the nonsolvent is greater than 30% (v/v), liquid-liquid phase separation between solvent and nonsolvent occurs quickly.

The aqueous acidic solution may be acetic acid, formic acid, hydrochloric acid, or sulfuric acid, wherein the amount of the aqueous acidic solution is in the range of 0.001 to 40% (v/v).

The freeze-drying may be performed at −196 to 0° C., but the temperature during the freeze-drying is not limited thereto. The freeze-drying time is not limited, and can be, for example, 6 hours or longer, or 12 hours or longer.

The amount of the chitosan may be in the range of 0.001 to 5% (w/v), and preferably 0.01 to 5% (w/v).

The aqueous acidic solution may further include at least one material selected from the group consisting of collagen, gelatin, fibronectin, lecithin, hyaluronic acid, alginic acid, poly-gamma-glutamic acid, beta-tricalcium phosphate and hydroxyapatite in addition to chitosan in order to improve biocompatibility of chitosan.

The method of producing a porous chitosan scaffold according to an embodiment of the present invention may further include neutralizing the aqueous acidic solution having chitosan and a solvent that does not dissolve the chitosan before freeze-drying the aqueous acidic solution. Here, the term "neutralizing" does not necessarily indicate the neutral pH but indicates raising the pH of the aqueous acidic solution, i.e., lessening the acidity. In general, the aqueous acidic chitosan solution has a relatively high acidity. Neutralizing in the aqueous acidic chitosan solution indicates lessoning a relatively high acidity of the aqueous acidic chitosan solution, for example chitosan aqueous acetic acid solution having a pH level of 2 to 3, to a relatively low acidity having a pH level of about pH 4.5 to 6.9. Chitosan is precipitated at pH levels in the range of 6.2 to 6.9 according to the amount of amine, and thus the acidity is lessened below the pH range at which chitosan is precipitated. The aqueous acidic chitosan solution can be neutralized by adding a solution having higher alkalinity than the aqueous acidic chitosan solution thereto. The alkaline solution may be selected from the group consisting of 0.001 to 2.0 M sodium hydroxide solution, 0.05 to 2.0 M ammonium hydroxide solution, 30 to 100% alcohol solution of 0.001 to 2.0 M sodium hydroxide, 30 to 100% alcohol solution of 0.05 to 2.0 M ammonium hydroxide, a reconstituted buffer solution (2.2 g of $NaHCO_3$, 4.77 g of HEPES (200 mM)/100 ml, 0.05 M of NaOH), and a 10× culture medium in which $NaHCO_3$ is removed (10× culture medium: DMEM:F12=3:1, Gibco BRL. DMEM-Cat. no. 12800-058, F12-Cat. no 21700-026), but is not limited thereto. For example, the aqueous acidic solution can be neutralized by immersing the obtained freeze-dried porous scaffold in excess of a neutralizing solution for 5 minutes to 1 hour, and sufficiently washing the porous scaffold with distilled water or a phosphate buffer solution having pH levels of 7.0 to 7.4.

The chitosan scaffold prepared according to the method of the present invention may be finally neutralized to have a pH in the vicinity of the neutral pH. The chitosan scaffold can be neutralized by adding an alkaline solution thereto or washing the acidic material in the chitosan scaffold. The alkaline solution may be selected from the group consisting of 0.01 to 2.0 M sodium hydroxide solution, 0.05 to 2.0 M ammonium hydroxide solution, 30 to 100% alcohol solution of 0.01 to 2.0 M sodium hydroxide, 30 to 100% alcohol solution of 0.05 to 2.0 M ammonium hydroxide, a reconstituted buffer solution (2.2 g of $NaHCO_3$, 4.77 g of HEPES (200 mM)/100 ml, 0.05 M of NaOH), and a 10× culture medium in which $NaHCO_3$ is removed (10× culture medium: DMEM:F12=3:1, Gibco BRL. DMEM-Cat. no. 12800-058, F12-Cat. no 21700-026), but is not limited thereto. Preferably, the alkaline solution may be 30 to 100% alcohol solution of 0.001 to 2.0 M sodium hydroxide, 30 to 100% alcohol solution of 0.05 to 2.0 M ammonium hydroxide.

Further, the chitosan scaffold can be washed at least twice with each of 98% or higher absolute ethanol, 80% ethanol solution, 70% ethanol solution, 60% ethanol solution, 50% ethanol solution, water and a buffer solution respectively in this order to completely remove excess of remaining acid and to be neutralized. The neutralization process can prevent the porous chitosan scaffold from rapidly shrinking.

The porous chitosan scaffold produced using the method according to the present invention has advantages of high tensile strength, uniform size distribution of pores, and excellent interconnectivity between the pores due to micropore formation. Accordingly, the chitosan scaffold produced using the method according to the present invention can be used as cell carriers used in tissue engineering including tissue regeneration, carriers used in cell culture, wound dressing and drug delivery, but the use of the chitosan scaffold is not limited thereto.

According to another aspect of the present invention, there is provided a chitosan scaffold used in tissue regeneration or cell culture.

BRIEF DESCRIPTION OF THE DRAWINGS

The patent or application file contains at least one drawing executed in color. Copies of this patent or patent application publication with color drawings will be provided by the office upon request and payment of the necessary fee.

The above and other features and advantages of the present invention will become more apparent by describing in detail exemplary embodiments thereof with reference to the attached drawings in which.

DETAILED DESCRIPTION OF THE INVENTION

Hereinafter, the present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

EXAMPLES

Comparative Example 1

Preparation of a Chitosan Scaffold by Freeze-Drying an Aqueous Acidic Chitosan Solution Chitosan (molecular weight: 760,000, degree of deacetylation: 80%) was added to 1% (v/v) of aqueous acetic acid solution to a concentration of 1% (w/v), and the mixture was stirred at room temperature for 24 hours to obtain a homogeneous aqueous acidic chitosan solution. 4 g of the aqueous acidic chitosan solution were placed in each of three sheet-shaped molds, then frozen at −70° C. for 24 hours, and freeze-dried in a refrigerator at −70° C. for 24 hours. As a result, a sheet-shaped scaffold was obtained. The scaffold was immersed in 100% ethanol and washed for 2 hours or longer to remove remaining acidic solution. Then, the resultant was sequentially washed with 90%, 80%, 70%, 60%, and 50% (v/v) ethanol solutions and distilled water respectively for longer than 1 hour. Then, the resultant was freeze-dried at −70° C. to obtain a final scaffold.

Figure 1:
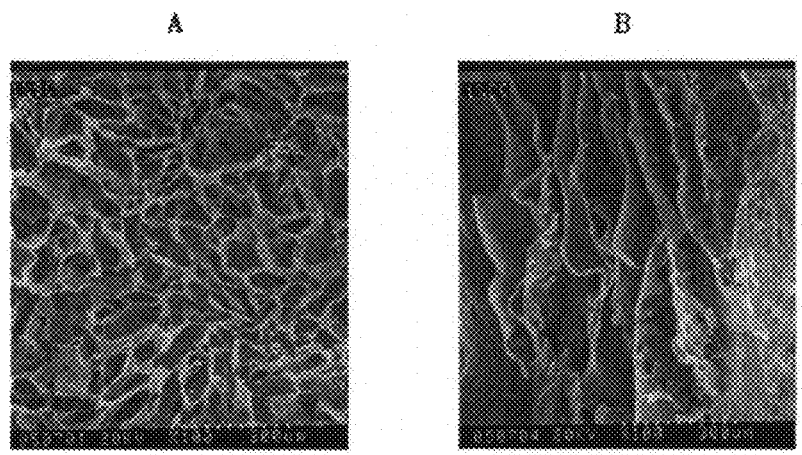
FIG. 1 is scanning electron microscope (SEM) photographs showing the surface and a cross section of a chitosan scaffold produced by freeze-drying an aqueous acidic chitosan solution.

FIG. 1 is SEM photographs showing the surface A and a cross section B of a chitosan scaffold produced by freeze-drying an aqueous acidic chitosan solution (×100). As illustrated in FIG. 1, each of pores in the chitosan scaffold is not linked to each other.

Example 1

Preparation of a Chitosan Scaffold by Freeze-drying an Aqueous Acidic Chitosan Solution Including n-butanol Chitosan (molecular weight: 760,000, degree of deacetylation: 80%) was added to 0.5%, 1%, and 2% (v/v) of aqueous acetic acid solutions to a concentration of 2% (w/v), and the mixtures were stirred at room temperature for 24 hours to obtain homogeneous aqueous acidic chitosan solutions (Reagent A). Then, n-butanol was added to 0.5%, 1%, and 2% aqueous acetic acid solutions to concentrations of 10%, 20%, and 40% respectively (Reagent B). 2 g of Reagent A having different concentrations of acetic acid were placed in each of three sheet-shaped molds, and 2 ml of Reagent B having different concentrations of n-butanol were respectively added thereto. The mixtures were reacted at room temperature for 1 hour, then frozen at −70° C. for 24 hours, and freeze-dried again at −70° C. for longer than 24 hours to respectively prepare porous chitosan scaffolds. The prepared porous chitosan scaffolds were washed in the same manner as in Comparative Example 1, and freeze-dried. The porous chitosan scaffold was gold-coated using a sputter-coater (Eiko IB3, Tokyo, Japan) for 5 minutes, and the surface changes and changes in the pore structure of the porous chitosan scaffold were observed using an electron microscope (Hitachi, Tokyo, Japan) at 20 kV according to the amount of acetic acid and butanol. Further, micropore formation and size distribution of pores were measured using mercury impregnation method.

Figure 2A:
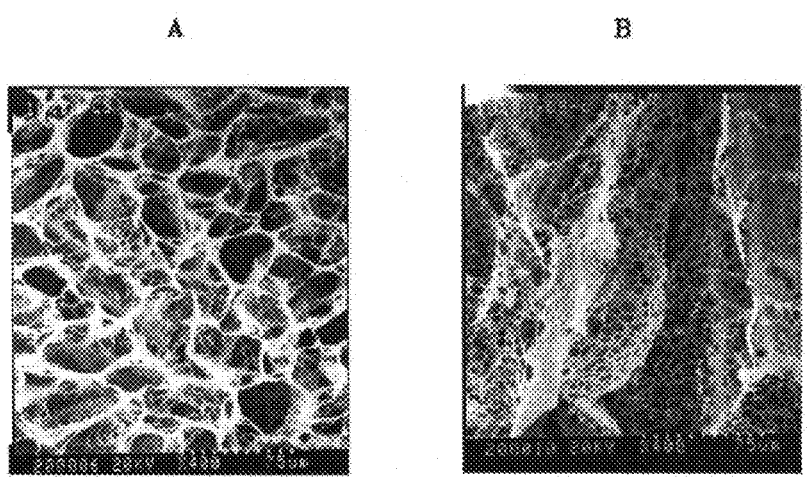
FIGS. 2A, 2B and 2C are SEM photographs showing the surfaces and cross sections of chitosan scaffolds produced by freeze-drying aqueous acidic chitosan solutions including n-butanol.
Figure 2B:
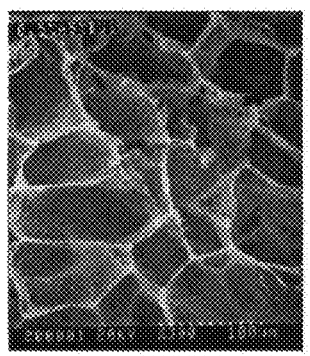
Figure 2B:
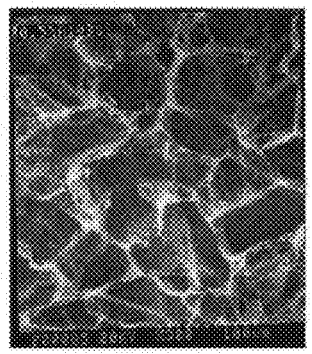
Figure 2C:
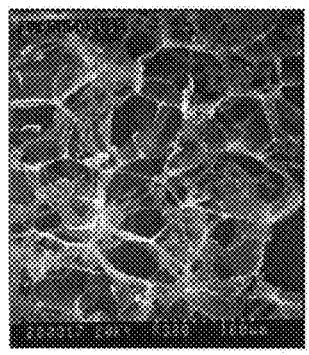
Figure 2C:
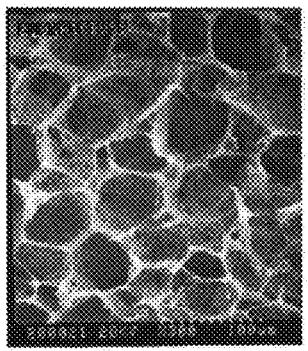

FIGS. 2A, 2B and 2C are SEM photographs showing the surfaces and cross sections of chitosan scaffolds produced by freeze-drying aqueous acidic chitosan solutions including n-butanol. A and B in FIG. 2A denote the surface and a cross section of a chitosan scaffold produced using a solution of acetic acid and butanol (acetic acid/butanol=1%/10%) (×400). C and D in FIG. 2B and E and F in FIG. 2C denote the surfaces and cross sections of a chitosan scaffold respectively produced using solutions of acetic acid and butanol (acetic acid/butanol=0.5%/5%, 0.5%/10%, 2%/5% and 2%/10%) (×300).

As illustrated in FIGS. 2A, 2B and 2C, the size of pores can be controlled to be from 30 to 100 μm according to the concentration of acetic acid and butanol. Further, when the concentration of butanol was varied from 5 to 10% in each of the acetic acid having 0.5% and 2%, the quantity of micropores increased to obtain an improved multi-space connecting structure. In particular, the tubal porous inner wall having the pore size of 80 μm or greater had micropores having the size of about 3 to 4 μm, and thus improved interconnectivity between the pores was identified.

Figure 3:
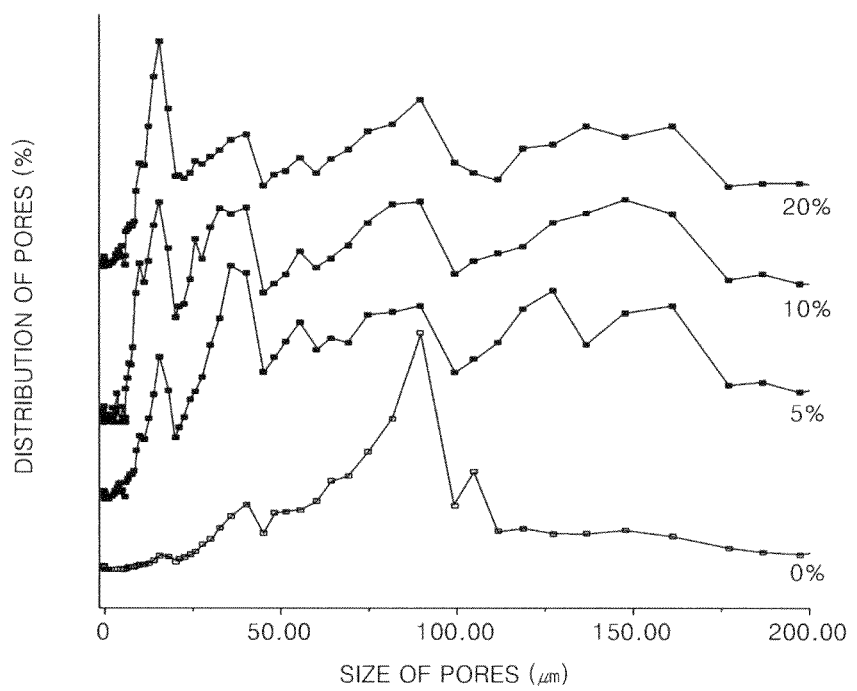
FIG. 3 is a graph illustrating measuring results of the size distribution of pores of a chitosan scaffold produced by freeze-drying an aqueous acidic chitosan solution including n-butanol using a porosimeter using mercury impregnation method.

FIG. 3 is a graph illustrating measuring results of the size distribution of pores of a chitosan scaffold produced by freeze-drying an aqueous acidic chitosan solution including n-butanol using a porosimeter using mercury impregnation method. As shown in FIG. 3, as the amount of n-butanol, which is a nonsolvent, increased, the quantity of micropores having the size of 4 μm and pores having the size of 10 to 17 μm increased compared to the chitosan scaffold produced by freeze-drying the aqueous acidic chitosan solution. On the other hand, the quantity of pores having the size of 30 to 45 μm decreased. That is, the size distribution of pores in the porous scaffold can be controlled by adjusting the concentration of n-butanol, and interconnectivity between the pores can be improved by controlling the distribution of micropores. In FIG. 3, the expressions of 0%, 5%, 10% and 20% indicate solutions having 1% of acetic acid, and 1% of chitosan, in which 0%, 5%, 10% and 20% of butanol were respectively added.

Comparative Example 2

Preparation of a Chitosan Scaffold by Freeze-Drying an Aqueous Acidic Chitosan Solution Chitosan (molecular weight: 760,000, degree of deacetylation: 85%) was added to 0.1% (v/v) of aqueous acetic acid solution to a concentration of 1% (w/v), and the mixture was stirred at room temperature for 24 hours to obtain a homogeneous aqueous acidic chitosan solution. The aqueous acidic chitosan solution was added drop wise to liquid nitrogen at −196° C. using an injector to give chitosan beads. The beads were freeze-dried at −70° C. for 48 hours. As a result, a porous chitosan bead-type scaffold was obtained. The scaffold was immersed in 100% ethanol and washed for 2 hours to remove excess of the solvent. Then, the resultant was sequentially washed twice with 90%, 80%, 70%, 60%, and 50% (v/v) ethanol solutions and distilled water respectively for 1 hour. Then, the resultant was frozen at −70° C. for 48 hours, and freeze-dried at −70° C. for 48 hours to obtain a final scaffold.

The chitosan bead-type scaffold were gold-coated using a sputter-coater (Eiko IB3, Tokyo, Japan), and the surface and pores in the chitosan bead-type scaffold were observed using a scanning electron microscope (Hitachi, Tokyo, Japan) at 20 kV.

Figure 4:
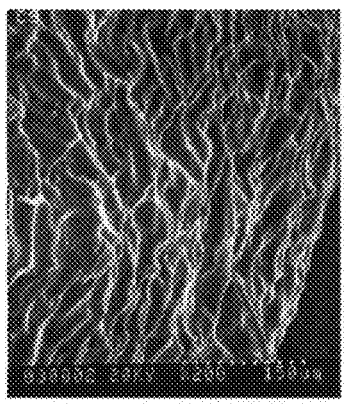
FIG. 4 is SEM photographs showing the surface and a cross section of a chitosan bead-type scaffold produced by freeze-drying an aqueous acidic chitosan solution.
Figure 4:
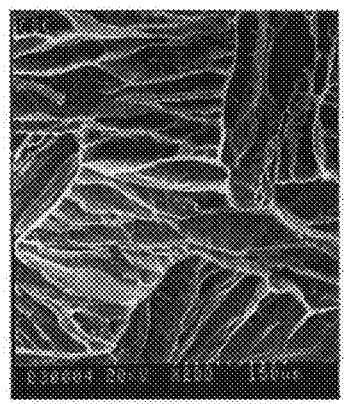

FIG. 4 is SEM photographs showing the surface A and a cross section B of a chitosan bead-type scaffold produced by freeze-drying an aqueous acidic chitosan solution (×200). As illustrated in FIG. 4, a porous structure of the surface is partially blocked, and a bead-type scaffold having multi-space connecting structure cannot be obtained since the inner walls do not have interconnectivity although the cross section has porosity.

Example 2

Preparation of a Chitosan Scaffold by Freeze-Drying an Aqueous Acidic Chitosan Solution Including n-butanol Chitosan (molecular weight: 760,000, degree of deacetylation: 85%) was added to 0.1% (v/v) of aqueous acetic acid solution to a concentration of 2% (v/v), and the mixture was stirred at room temperature for 24 hours to obtain a homogeneous aqueous acidic chitosan solution (Reagent A). Then, n-butanol was added to 0.1% (v/v) of aqueous acetic acid solution to a concentration of 30% (v/v) (Reagent B). 2 g of Reagent A were placed in each of three beakers, and 2 ml of Reagent B were respectively added to the beakers. The mixtures were reacted at room temperature for 10 hours, and added drop wise to liquid nitrogen at −196° C. using an injector to obtain chitosan beads. The beads were freeze-dried at −70° C. for 48 hours. As a result, a porous chitosan bead-type scaffold was obtained. The scaffold was immersed in 100% ethanol and washed for 2 hours to remove excess of the solvent. Then, the resultant was sequentially washed twice with 90%, 80%, 70%, 60%, and 50% (v/v) ethanol solutions and distilled water respectively for 1 hour. Then, the resultant was freeze-dried at −70° C. for 48 hours to obtain a final scaffold.

The chitosan bead-type scaffold were gold-coated using a sputter-coater (Eiko IB3, Tokyo, Japan), and the surface and pores in the chitosan bead-type scaffold were observed using a scanning electron microscope (Hitachi, Tokyo, Japan) at 20 KV.

Figure 5:
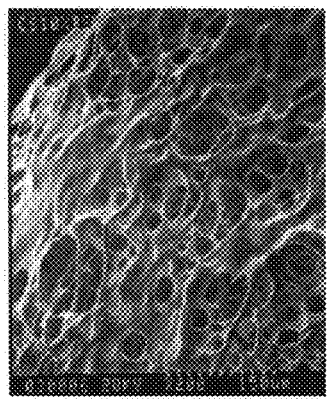
FIG. 5 is SEM photographs showing the surface and a cross section of a chitosan bead-type scaffold produced by freeze-drying an aqueous acidic chitosan solution including n-butanol.
Figure 5:
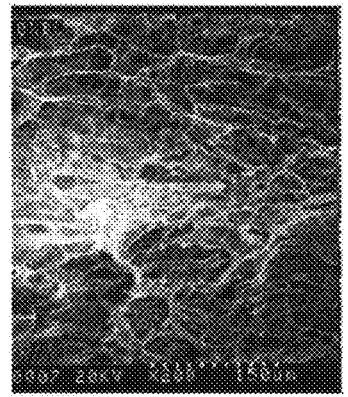

FIG. 5 is SEM photographs showing the surface A and a cross section B of a chitosan bead-type scaffold produced by freeze-drying an aqueous acidic chitosan solution including n-butanol (×200). As illustrated in FIG. 5, it was observed that pores were completely open on the surface due to n-butanol addition and improved multi-space connecting structure was obtained in the cross section of the beads since the inner walls in the pores include micropores, which is distinguished from the results observed in FIG. 4

Example 3

Preparation of a Chitosan Scaffold by Freeze-Drying an Aqueous Acidic Chitosan Solution Including Acetone Acetone was added to 5% (v/v) sulfuric acid solution to a concentration of 8% (v/v) to prepare an 8% (v/v) acidic acetone solution. Chitosan (molecular weight: 70,000, degree of deacetylation: 76%) was added to the acidic acetone solution to a concentration of 1% (v/v), and the mixture was stirred at room temperature for 24 hours to obtain a homogeneous aqueous acidic chitosan solution. Then, 4 g of the aqueous acidic chitosan solution were placed in each of three cylindrical molds, and placed in a refrigerator at −100° C. for 48 hours, and the resultant was freeze-dried at −70° C. for 24 hours. As a result, a cylindrical porous chitosan scaffold was obtained. The scaffold was washed three times with 100% ethanol to remove excess of the solvent. Then, the resultant was sequentially washed twice with 90%, 80%, 70%, 60%, and 50% (v/v) ethanol solutions and distilled water respectively for 1 hour or longer. Then, the resultant was freeze-dried at −70° C. to obtain a final scaffold.

As a result, it was observed that pores were completely open on the surface due to acetone addition and improved multi-space connecting structure was obtained in the cylindrical porous chitosan scaffold since the inner walls in the pores include micropores (not shown).

Example 4

Preparation of a Chitosan Scaffold by Freeze-Drying an Aqueous Acidic Chitosan Solution Including Iso-hexanol Chitosan (molecular weight: 70,000, degree of deacetylation: 76%) was added to 1% (v/v) of aqueous acetic acid solution to a concentration of 2% (w/v), and the mixture was stirred at room temperature for 24 hours to obtain a homogeneous aqueous acidic chitosan solution. 0.1% (w/v) of collagen (Type Ip collagen, Cellmatrix, Gelatin Corp., Osaka) was gradually added thereto while stirring to obtain a homogeneous aqueous chitosan solution (Reagent A). Then, iso-hexanol was added to 1% aqueous acetic acid solution to a concentration of 20% (w/v) (Reagent B). 2 g of Reagent A were placed in each of three molds, and 2 ml of Reagent B were respectively added to the molds. The mixtures were placed at 5° C. for 5 hours, placed in a refrigerator at −60° C. for 72 hours, and freeze-dried at −70° C. for 24 hours. As a result, a porous chitosan scaffold was obtained.

The porous chitosan scaffold was neutralized in 0.1 N sodium hydroxide solution for 3 hours to remove excess of the solvent, and sufficiently washed with excess of distilled water until the remaining solution became the neutral. Then, the resultant was freeze-dried at −70° C. to obtain a final scaffold.

Then, the scaffold was prepared into slices having the thickness of 5 μm using paraffin blocks, and the slices were dyed with eosin.

Figure 6:
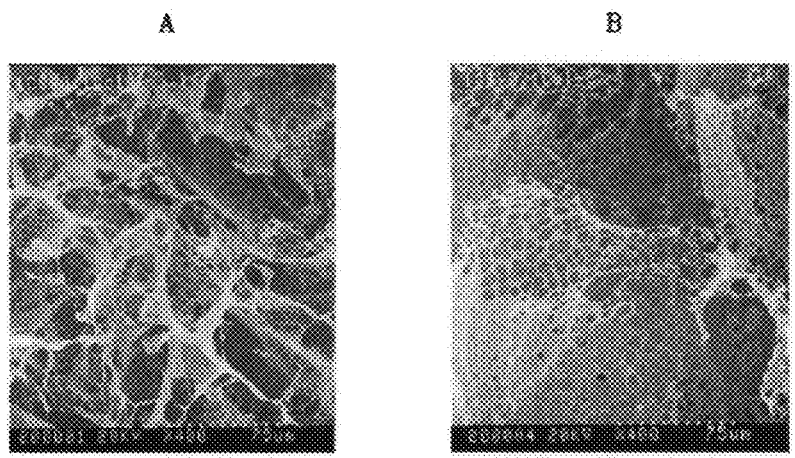
FIG. 6 is SEM photographs showing the surface and a cross section of a chitosan-collagen scaffold produced by freeze-drying a solution including 2% (w/v) of an acidic chitosan containing iso-hexanol and 0.1% (w/v) of collagen.

FIG. 6 is SEM photographs showing the surface A and a cross section B of a chitosan-collagen scaffold produced by freeze-drying a solution including 2% (v/v) of an acidic chitosan containing iso-hexanol and 0.1% (w/v) of collagen (×400). As illustrated in FIG. 6, the size and size distribution of pores were uniform regardless of collagen addition, micropores were observed in pores, and the pores are well connected to each other in the cross section. The size of pore was proper for tissue engineering application.

Figure 7:
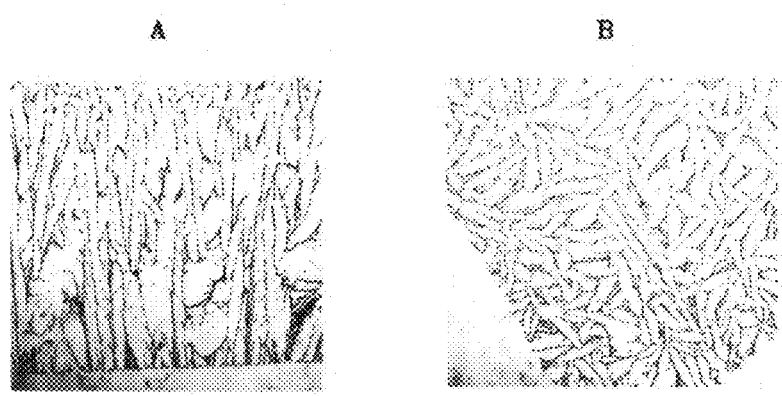
FIG. 7 is photographs showing the porous surface and a cross section of a slice of a chitosan-collagen scaffold produced by freeze-drying a solution including 2% (w/v) of an acidic chitosan containing iso-hexanol and 0.1% (w/v) of collagen, and dyed with eosin.

FIG. 7 is photographs showing the porous surface A and a cross section B of a slice of a chitosan-collagen scaffold produced by freeze-drying a solution including 2% (w/v) of an acidic chitosan containing iso-hexanol and 0.1% (w/v) of collagen, and dyed with eosin that selectively dyes collagen showing effects of collagen (×50). As illustrated in FIG. 7, regions colored brown indicate dyed collagen, the size and size distribution of pores were uniform regardless of collagen addition as illustrated in SEM photographs of FIG. 6. The size of pores was proper for tissue engineering application.

Example 5

Preparation of a Chitosan Scaffold by Freeze-Drying an Aqueous Acidic Chitosan Solution Including Ethylene Glycol Monoethylether Chitosan (molecular weight: 50,000, degree of deacetylation: 76%) was added to 0.1 N hydrochloric acid solution to a concentration of 1.5%, and the mixture was occasionally stirred at 5° C. for 24 hours to obtain a homogeneous aqueous acidic chitosan solution. 1% hydroxyapatite and 1% beta-tricalcium phosphate were added thereto to obtain uniform chitosan solutions (Reagent A). Then, ethylene glycol monoethylether was added to 0.1 N hydrochloric acid solution to a concentration of 10% (w/v) (Reagent B). 2 g of Reagent A were placed in each of three molds, and 2 ml of Reagent B were respectively added thereto. The mixtures were reacted at 5° C. for 5 hours, placed in a refrigerator at −60° C. for 72 hours, and freeze-dried again at −70° C. for 24 hours. As a result, a porous chitosan scaffold was obtained.

The porous chitosan scaffold was neutralized in 0.1 N sodium hydroxide solution for 3 hours to remove excess of the solvent, and sufficiently washed with excess of distilled water until the remaining solution became the neutral. Then, the resultant was freeze-dried at −70° C. to obtain a final scaffold, and the obtained final scaffold was used in cytocompatibility tests.

Example 6

Cytocompatibility of Porous Chitosan Scaffolds

Cytocompatibility of chitosan scaffolds produced according to Comparative Examples 1 and 3, and Examples 1, 4 and 5 for human fibroblasts and rabbit cartilage cells were examined.

(1) Cytocompatibility of Chitosan Scaffolds Produced According to Comparative Examples 1 and 3, and Examples 1 and 4 for Human Fibroblasts Fibroblasts were separated from dermis of foreskin in a human infant and cultured in an F-medium (DMEM: F-12=3:1, 10% FBS, 1% penicillin-streptomycin). The chitosan scaffolds produced according to Comparative Examples 1 and 3, and Examples 1 and 4 were sterilized with 70% ethanol for 48 hours before fibroblast inoculation, washed twice with a phosphate buffer solution and once with a culture medium, and placed in 48 well plates. The cultured human fibroblasts (P=3) were inoculated into the chitosan scaffolds at a concentration of 50,000 cell/ml/well.

The inoculated fibroblast cells were cultured in a medium (DMEM:F12=3:1, Gibco BRL. DMEM-catalog no. 12800-058, F12-catalog no. 21700-026) including 10% fetal bovine serum (JRH Biosciences catalog no. 12103-78P) in an incubator under 95% humidity at 37° C., with 5% $CO_2$ for 4 hours for cell attachment. Then, they were cultured for one day while the culture medium was added to the extent that the chitosan scaffold is not dried. The next day, the culture medium was added to the extent that the chitosan scaffold is completely immersed, and then the chitosan scaffold to which the fibroblasts were attached was continuously cultured. After they were cultured for 6 hours, 2 days, 4 days, and 7 days while the culture medium was changed once every 2 days, the culture medium was removed. 500 μl of a mixture of cell counting kit −8 dye ((2-(2-methoxy-4-nitrophenyl)-3-(4-nitrophenyl)-5-(2,4-disulfophenyl)-2H-tetrazolium, monosodium salt), DOJINDO, JAPAN) and culture medium (1:9 v/v) was added to each of the wells and they were cultured in an incubator at 37° C. with 5% $CO_2$ for 3 hours. A chitosan scaffold in which fibroblasts were not inoculated was used as the control group. Each of 100 μl of orange culture mixture colored by the cell counting kit-8 was placed in a 96 well plate. Absorbance was measured at 405 nm using a microplate ELISA reader (Molecular Devices, USA) to identify the degree of proliferation of cells. The results are shown in FIG. 8.

Figure 8:
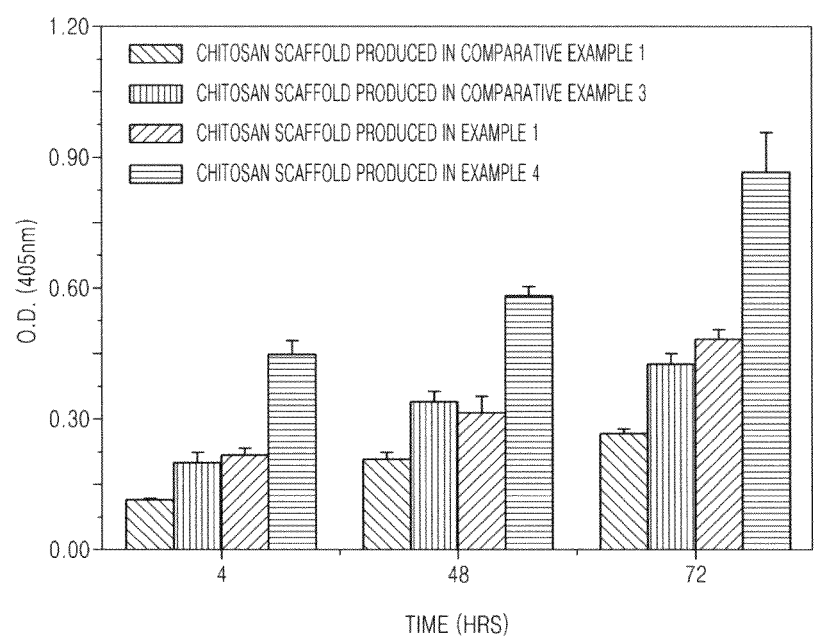
FIG. 8 is a graph illustrating cytocompatibility of chitosan scaffolds produced according to Comparative Example 1, Example 1, Example 4, and Comparative Example 3 for fibroblasts.

FIG. 8 is a graph illustrating cytocompatibility of chitosan scaffolds produced according to Comparative Example 1, Examples 1 and 4 and Comparative Example 3 for fibroblasts. As illustrated in FIG. 8, fibroblast growth increased in the chitosan scaffold produced according to Example 1 in which interconnectivity is improved between pores and micropores compared to the chitosan scaffold produced according to Comparative Example 1, and fibroblast growth increased by more than 82% after 3 days. In particular, the chitosan scaffold produced according to Example 1 had the same effect on fibroblasts in the beginning compared to the chitosan scaffold produced according to Comparative Example 3 in which collagen that is known to have excellent biocompatibility was added. However, after 3 days, fibroblasts in the chitosan scaffold of Example 1 grew 13.6% higher compared to those in the chitosan scaffold to which collagen was added. Further, fibroblast growth in the chitosan scaffold produced according to Example 4 increased by greater than 73% and 104% respectively after 2 days and 3 days compared to fibroblast growth in the chitosan scaffold produced according to Comparative Example 3 to which collagen was simply added. Thus, when collagen is added to the porous chitosan scaffold produced according to the present invention, biocompatibility of the porous chitosan scaffold is improved.

(2) Cytocompatibility of Chitosan Scaffolds Produced According to Comparative Example 1 and Example 5 for Rabbit Cartilage Cells Cartilage cells were separated from rabbit costal cartilage. The separated cartilage cells were treated with trypsin after being cultured to about 80% confluency at p=1 and cultured in a medium (MSCGM catalog no. 12800-058, F12-catalog no. 21700-026) including 10% fetal bovine serum (JRH Biosciences catalog no. 12103-78P) and 1 ng/ml b-FGF. The chitosan scaffolds produced according to Comparative Example 1 and Example 5 were sterilized with 70% ethanol for 48 hours before cartilage cell inoculation, washed twice with a phosphate buffer solution and once with a culture medium, and placed in 48 well plates. The cultured cartilage cells were inoculated into the chitosan scaffolds at a concentration of 5,000 cell/scaffold.

The inoculated cartilage cells were cultured in a medium (MSCGM catalog no. 12800-058, F12-catalog no. 21700-026) including 10% fetal bovine serum (JRH Biosciences catalog no. 12103-78P) and 1 ng/ml b-FGF in an incubator under 95% humidity at 37° C., with 5% $CO_2$ for 4 hours for cell attachment. Then, They were cultured for one day while the culture medium was added to the extent that the chitosan scaffold is not dried. The next day, the culture medium was added to the extent that the chitosan scaffold is completely immersed, and then the chitosan scaffold were attached was continuously cultured. After they were cultured for 6 hours, 2 days, 4 days, and 7 days while the culture medium was changed once every 2 days, the culture medium was removed. 500 μl of a mixture of cell counting kit −8 dye ((2-(2-methoxy-4-nitrophenyl)-3-(4-nitrophenyl)-5-(2,4-disulfophenyl)-2H-tetrazolium, monosodium salt), DOJINDO, JAPAN)

and culture medium (1:9 v/v) was added to each of the wells and they were cultured in an incubator at 37° C. with 5% $CO_2$ for 3 hours. A chitosan scaffold in which cartilage cells were not inoculated was used as the control group. 100 μl of orange culture mixture colored by the cell counting kit-8 were placed in a 96 well plate. Absorbance was measured at 405 nm using a microplate ELISA reader (Molecular Devices, USA) to identify the degree of proliferation of cells. The results are shown in FIG. 9.

Figure 9:
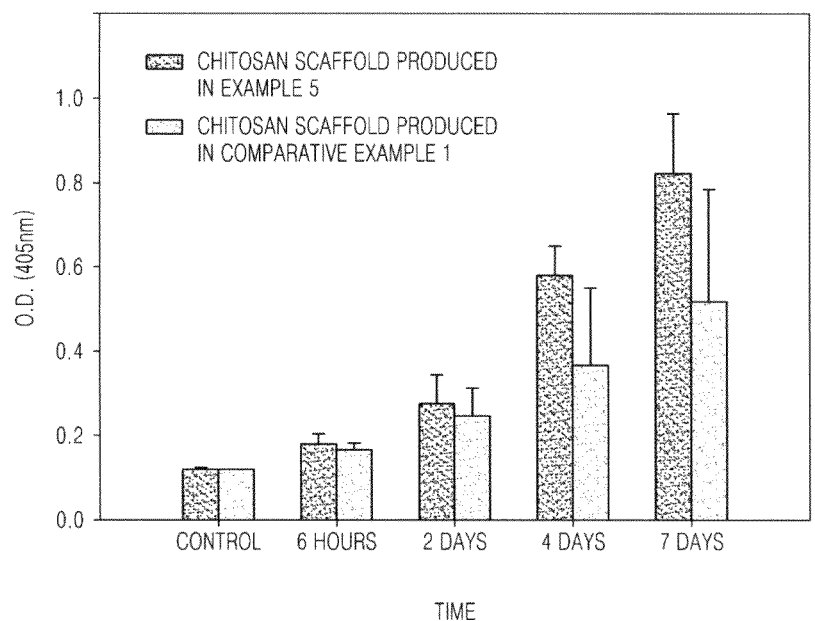
FIG. 9 is a graph illustrating cytocompatibility of chitosan scaffolds produced according to Comparative Example 1 and Example 5 for cartilage cells.

FIG. 9 is a graph illustrating cytocompatibility of chitosan scaffolds produced according to Comparative Example 1 and Example 5 for cartilage cells. As illustrated in FIG. 9, the cartilage cell growth in the chitosan scaffold produced according to Example 5 was almost the same in the beginning, but increased by greater than 11% after 2 days, and further by greater than 58% and 60% respectively after 4 days and 7 days compared to the cartilage cell growth in the chitosan scaffold produced according to Comparative Example 1.

Therefore, the chitosan scaffold produced according to the present invention has micropores, and excellent interconnectivity between pores, and thus have excellent properties facilitating cell growth as a cell support.

According to the method of the present invention, a chitosan scaffold having high tensile strength in which size and size distribution of pores are uniform and the pores are linked to each other can be obtained.

The chitosan scaffold of the present invention can be effectively used in proliferating cells for tissue regeneration, and used as a support for culturing cells.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing a porous chitosan scaffold, the method comprising:
providing an aqueous acidic solution comprising:
chitosan, and
a solvent which does not dissolve the chitosan,
wherein the solvent which does not dissolve the chitosan is selected from the group consisting of a C3-C8 aliphatic alcohol having one hydroxy group, ethylene glycol monoethylether, ethylene glycol monobutylether, dioxane, tetrahydrofuran, dimethylcarbonate, acetone and acetonitrile, and the amount of the solvent which does not dissolve the chitosan is in the range of 0.001 to 30% (v/v), based on the volume of the solution; and
freeze-drying the aqueous acidic solution to form a porous chitosan scaffold,
wherein the solvent which does not dissolve the chitosan is present during freeze-drying.

2. The method of claim 1, wherein the aqueous acidic solution is selected from the group consisting of acetic acid, formic acid, hydrochloric acid, and sulfuric acid, the amount of which is in the range of 0.001 to 40% (v/v).

3. The method of claim 1, wherein the freeze-drying is performed at −196 to 0° C.

4. The method of claim 1, wherein the amount of the chitosan is in the range of 0.001 to 5% (w/v).

5. The method of claim 1, wherein the aqueous acidic solution further comprises at least one material selected from the group consisting of collagen, gelatin, fibronectin, lecithin, hyaluronic acid, alginic acid, poly-gamma-glutamic acid, beta-tricalcium phosphate and hydroxyapatite.

6. The method of claim 1 further comprising
neutralizing to a pH below the pH range at which chitosan is precipitated the aqueous acidic solution comprising chitosan and the solvent before freeze-drying the aqueous acidic solution.

7. The method of claim 6, wherein the neutralized solution has a pH level of 4.5 to 6.9.

* * * * *